US010677771B2

(12) United States Patent
Dittberner et al.

(10) Patent No.: US 10,677,771 B2
(45) Date of Patent: Jun. 9, 2020

(54) DETECTING GAS LEAKS USING UNMANNED AERIAL VEHICLES

(71) Applicant: INTERNATIONAL BUSINESS MACHINES CORPORATION, Armonk, NY (US)

(72) Inventors: Matthias Dittberner, Neustrelitz (DE); Levente Klein, Tuckahoe, NY (US); Jason D. Renwick, Santa Cruz (TT)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 269 days.

(21) Appl. No.: 15/800,116

(22) Filed: Nov. 1, 2017

(65) Prior Publication Data

US 2018/0292286 A1 Oct. 11, 2018

Related U.S. Application Data

(63) Continuation of application No. 15/479,325, filed on Apr. 5, 2017.

(51) Int. Cl.
*G01N 33/00* (2006.01)
*G05D 1/00* (2006.01)
(Continued)

(52) U.S. Cl.
CPC ....... *G01N 33/0047* (2013.01); *B64C 39/024* (2013.01); *G01C 21/00* (2013.01);
(Continued)

(58) Field of Classification Search
CPC ....... G01N 33/0047; G01N 2021/0143; G01N 2021/1795; G01N 2201/0214;
(Continued)

(56) References Cited

U.S. PATENT DOCUMENTS

2001/0028032 A1 10/2001 Church et al.
2006/0268947 A1* 11/2006 Kalayeh ............ G01N 21/3504
372/20
(Continued)

FOREIGN PATENT DOCUMENTS

CN 204832867 U * 12/2015
CN 106501829 A * 3/2017
(Continued)

OTHER PUBLICATIONS

English Translation: Wang, Chinese Patent Publication CN 106501829 A, dated Mar. 15, 2017, Chinese Patent Office (Year: 2017).*
(Continued)

*Primary Examiner* — Nadeem Odeh
(74) *Attorney, Agent, or Firm* — Cantor Colburn LLP; Vazken Alexanian

(57) ABSTRACT

Methods, systems and computer program products for detecting gas leaks using a drone are provided. Aspects include capturing a first set of data regarding a presence of a gas in the geographic area while flying along the initial flight path. Aspects also include creating secondary flight paths through regions in the geographic area in which the presence of the gas exceeds a threshold amount and capturing a second set of data regarding a concentration of the gas in the one or more regions while flying along the secondary flight paths. Aspects further include capturing wind data while flying along the initial and second flight paths and creating a three-dimensional gas plume model for gas leaks identified in the geographic area based on the first set of data, the second set of data and the wind data, wherein the three-dimensional gas plume model identifies a source of the gas leaks.

8 Claims, 10 Drawing Sheets

(51) Int. Cl.

| | |
|---|---|
| *B64C 39/02* | (2006.01) |
| *G08G 5/00* | (2006.01) |
| *G01N 21/3504* | (2014.01) |
| *G06T 17/05* | (2011.01) |
| *G06K 9/00* | (2006.01) |
| *G05D 1/10* | (2006.01) |
| *G06K 9/20* | (2006.01) |
| *G01C 21/00* | (2006.01) |
| *G01M 3/04* | (2006.01) |
| *G06T 7/73* | (2017.01) |
| *G01N 21/17* | (2006.01) |
| *G01N 21/01* | (2006.01) |

(52) U.S. Cl.
CPC .......... *G01M 3/04* (2013.01); *G01N 21/3504* (2013.01); *G05D 1/0088* (2013.01); *G05D 1/0094* (2013.01); *G05D 1/101* (2013.01); *G06K 9/0063* (2013.01); *G06K 9/00201* (2013.01); *G06K 9/2018* (2013.01); *G06T 17/05* (2013.01); *G08G 5/0013* (2013.01); *G08G 5/0021* (2013.01); *G08G 5/0034* (2013.01); *G08G 5/0039* (2013.01); *G08G 5/0069* (2013.01); *G08G 5/0086* (2013.01); *B64C 2201/024* (2013.01); *B64C 2201/123* (2013.01); *B64C 2201/127* (2013.01); *B64C 2201/141* (2013.01); *G01N 2021/0143* (2013.01); *G01N 2021/1795* (2013.01); *G01N 2201/0214* (2013.01); *G06T 7/73* (2017.01); *G06T 2207/10032* (2013.01); *G06T 2207/10048* (2013.01); *G06T 2207/30181* (2013.01)

(58) Field of Classification Search
CPC ..... G01N 21/3504; G01C 21/00; G01M 3/04; G05D 1/101; G05D 1/0094; G05D 1/0088; G06T 2207/30181; G06T 7/73; G06T 2207/10032; G06T 2207/10048; G06T 17/05; B64C 2201/024; B64C 2201/127; B64C 2201/141; B64C 2201/123; B64C 39/024; G06K 9/00201; G06K 9/2018; G06K 9/0063; G08G 5/0013; G08G 5/0021; G08G 5/0034; G08G 5/0039; G08G 5/0086; G08G 5/0069
USPC .......................................................... 701/3
See application file for complete search history.

(56) References Cited

U.S. PATENT DOCUMENTS

| | | | |
|---|---|---|---|
| 2009/0222207 A1* | 9/2009 | Bernhardt | G01J 3/42 702/2 |
| 2015/0323449 A1 | 11/2015 | Jones et al. | |
| 2015/0336667 A1* | 11/2015 | Srivastava | B64C 39/024 701/2 |
| 2016/0202225 A1 | 7/2016 | Feng et al. | |
| 2016/0214715 A1 | 7/2016 | Meffert | |
| 2017/0097274 A1* | 4/2017 | Thorpe | G01B 21/20 |
| 2018/0188129 A1* | 7/2018 | Choudhury | G01M 3/04 |
| 2018/0209902 A1* | 7/2018 | Myshak | G01N 21/3504 |
| 2018/0284088 A1* | 10/2018 | Verbeck, IV | G01N 1/26 |

FOREIGN PATENT DOCUMENTS

| | | | |
|---|---|---|---|
| WO | 2007103644 A2 | 9/2007 | |
| WO | 2011015855 A1 | 2/2011 | |
| WO | 2011086357 A1 | 7/2011 | |
| WO | WO-2016029305 A1 * | 3/2016 | ......... G01N 21/3504 |

OTHER PUBLICATIONS

English Translation: Duan, Chinese Patent Publication CN 204832867 U, dated Dec. 2, 2015, Chinese Patent Office (Year: 2015).*
Bing et al., Three-Dimensional Gas Distribution Mapping with a Micro-Drone, Jul. 2015, IEEE, 34th Chinese Control Conference (CCC) (Year: 2015).*
Enviropedia, Volatile Organic Compounds, Mar. 3, 2016, Enviropedia Online Website (<http://www.enviropedia.org.uk/Air_Quality/VOCs.php>) (Year: 2016).*
Malaver et al., Development and Integration of a Solar Powered Unmanned Aerial Vehicle and a Wireless Sensor Network to Monitor Greenhouse Gases, Feb. 2015, Multidisciplinary Digital Publishing Institute (MDPI) Sensors Feb. 2015 (Year: 2015).*
Reggente et al., Using Local Wind Information for Gas Distribution Mapping in Outdoor Environments with a Mobile Robot, Oct. 2009, 2009 IEEE Sensors (Year: 2009).*
Reggente et al., The 3D-Kernal DM+V/W Algorithm, Using Wind Information in Three Dimensional Gas Distribution Modeling with a Mobile Robot, Nov. 2010, 2010 IEEE Sensors (Year: 2010).*
Letheren et al., Design and Flight Testing of a Bio-Inspired Plume Tracking Algoirthm for Unmanned Aerial Vehicles, Mar. 2016, IEEE Aerospace Conference 2016 (Year: 2016).*
Dittberner et al., "Detecting Gas Leaks Using Unmanned Aerial Vehicles"; U.S. Appl. No. 15/479,325; filed Apr. 5, 2017.
List of IBM Patents or Patent Applications Treated as Related; (Appendix P), Date Filed Nov. 1, 2017; 2 pages.
Bretschneider, et al. "UAV-Based Gas Pipline Leak Detection", Conference Paper, Oct. 2014, https://www.researchgate.net/publication/275035983; ResearchGate, 7 pgs.

* cited by examiner

DETECTING GAS LEAKS USING UNMANNED AERIAL VEHICLES

DOMESTIC PRIORITY

This application is a continuation of U.S. patent application Ser. No. 15/479,325, filed Apr. 5, 2017, the disclosure of which is incorporated by reference herein in its entirety.

STATEMENT OF GOVERNMENT RIGHTS

This invention was made with Government support under Contract DE-AR0000540 awarded by the U.S. Department of Energy. The United States Government has certain rights in this invention.

BACKGROUND

The present invention relates generally to a system and method for detecting gas leaks using unmanned aerial vehicles and, more specifically, to a system and method for using unmanned aerial vehicles, also referred to herein as drones, to identify the source of a gas leak.

Global warming is accelerated by the presence of greenhouse gasses in the atmosphere. While the impact of Carbon Dioxide is well documented, less commonly known, Methane, ethane, nitric oxide, or hydrogen sulphide may not be as well documented. Many of the above gases may have a greenhouse gas impact much greater than that of carbon dioxide. One source of methane leaks come from is at natural gas extraction sites. In many cases, leaks can be easily fixed if monitoring and tracking technologies are in place to detect and alert an owner about the size and locations of the leaks. Not only do these leaks have a major environmental impact, they can present a health hazard. If these leaks go unregulated or undetected, these hazards can become potentially detrimental and also a present a major financial burden on the operating companies.

Currently, the detection of these leaks is a manual and tedious process that involves a person inspecting a methane site with an infrared camera. These inspections are infrequent and are in many cases not quantitative in determining the leak rate. In addition, theses inspections pose health risks to the personnel who are tasked with performing the inspections.

SUMMARY

Embodiments include methods and computer program products for detecting a gas leak with a drone are provided. The method includes capturing, by a drone, a first set of data regarding a presence of a gas in a geographic area while flying along an initial flight path through the geographic area and creating one or more secondary flight paths through one or more regions in the geographic area in which the presence of the gas exceeds a threshold amount. The method also includes capturing, by a drone, a second set of data regarding a concentration of the gas in the one or more regions while flying along the one or more secondary flight paths and capturing, by a drone, wind data in the geographic area while flying along the initial flight path and the one or more secondary flight paths. The method also includes creating a three-dimensional gas plume model for gas leaks identified in the geographic area based on the first set of data, the second set of data and the wind data, wherein the three-dimensional gas plume model identifies a location of a source of the gas leaks.

Embodiments include a drone for detecting a gas leak a geographic area. The drone includes a memory and a processor communicatively coupled to the memory, wherein the processor is configured to perform a method. The method includes capturing, by a drone, a first set of data regarding a presence of a gas in a geographic area while flying along an initial flight path through the geographic area and creating one or more secondary flight paths through one or more regions in the geographic area in which the presence of the gas exceeds a threshold amount. The method also includes capturing, by a drone, a second set of data regarding a concentration of the gas in the one or more regions while flying along the one or more secondary flight paths and capturing, by a drone, wind data in the geographic area while flying along the initial flight path and the one or more secondary flight paths. The method also includes creating a three-dimensional gas plume model for gas leaks identified in the geographic area based on the first set of data, the second set of data and the wind data, wherein the three-dimensional gas plume model identifies a location of a source of the gas leaks.

Additional features are realized through the techniques of the present invention. Other embodiments and aspects of the invention are described in detail herein and are considered a part of the claimed invention. For a better understanding of the invention with the features, refer to the description and to the drawings.

BRIEF DESCRIPTION OF THE DRAWINGS

The subject matter which is regarded as the invention is particularly pointed out and distinctly claimed in the claims at the conclusion of the specification. The forgoing and other features of embodiments of the invention are apparent from the following detailed description taken in conjunction with the accompanying drawings in which:

DETAILED DESCRIPTION

Embodiments include systems, methods and computer program products for detecting gas leaks using a drone, or unmanned aerial vehicle. In exemplary embodiments, a drone includes sensors including a camera, an infrared camera and one or more chemical sensors that are used to capture data regarding the presence of gas in the air above a geographic area. In exemplary embodiments, the drone can fly high above the geographic area and capture images and distance measurements that are used to create a three-dimensional model of the geographic area. The drone flies along a first flight path determined based on the three-dimensional model, through the geographic area and collects high-level information that indicates the presence of a gas leak.

In exemplary embodiments, one or more secondary flight plans are identified in regions that have higher than expected levels of detected gas based on the high-level information and the three-dimensional model. The drone then flies along the one or more secondary flight plans and collects detailed gas concentration data. A three-dimensional model of a gas plume gas in the geographical area is then created based on the collected gas concentration data and the three-dimensional model of the geographic area.

Figure 1:
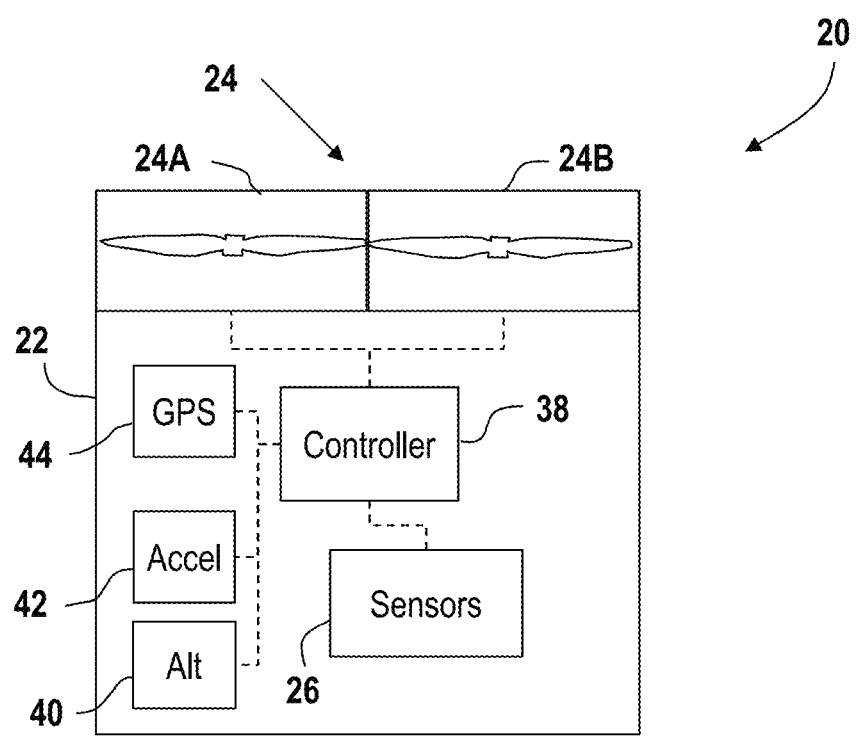
FIG. 1 depicts a block diagram of a drone in accordance with an embodiment.

Referring now to FIG. 1, an embodiment is shown of a drone 20 or unmanned aerial vehicle. As used herein, the term "drone" refers to an aerial vehicle capable of operating autonomously from a human operator to perform a predetermined function. The drone 20 includes a fuselage 22 that supports at least one thrust device 24. In an embodiment, the drone 20 includes a plurality of thrust devices 24A, 24B, such as four thrust devices arranged about the periphery of the fuselage 22. In an embodiment, the thrust devices 24 include propeller member that rotates to produce thrust. The thrust devices 24 may be configurable to provide both lift (vertical thrust) and lateral thrust (horizontal thrust). The vertical and horizontal components of the thrust allow the changing of the altitude, lateral movement and orientation (attitude) of the drone 20.

In the exemplary embodiment, the fuselage 22 and thrust devices 24 are sized and configured to carry a plurality of sensors 26. In exemplary embodiments, the sensors 26 can include image capture equipment, video capture equipment, audio capture equipment, depth capture equipment, or any other type of data capture equipment. In one embodiment, the sensors 26 include a camera, an infrared camera, and one or more gas sensors, such as a volatile organic compound (VOC) sensor that would be sensitive to methane, ethane and other chemical gases. In some embodiments, the sensors can include a variety of chemical sensors configured to detect the presence of specific compounds. In one embodiment, the VOC sensor can be sensitive to methane gas absorption and can be tuned to be selectively sensitive to change in methane concentration.

The drone 20 includes a controller 38 having a processing circuit. The controller 38 may include processors that are responsive to operation control methods embodied in application code such as those shown in FIGS. 6 and 7. These methods are embodied in computer instructions written to be executed by the processor, such as in the form of software. The controller 38 is coupled to transmit and receive signals from the thrust devices 24 to determine and change their operational states (for example adjust lift from thrust devices 24). The controller 38 may further be coupled to one or more devices that enable the controller to determine the position, orientation, and altitude of the drone 20. In an embodiment, these devices include an altimeter 40, a gyroscope or accelerometers 42 or a global positioning satellite (GPS) system 44. The controller 38 is further coupled to the one or more sensors 26. In exemplary embodiments, the drone 20 is configured to simultaneously detect the presence of a chemical compound, such as the methane gas, while recording its GPS location.

In exemplary embodiments, the drone 20 includes a camera that captures images that are processed with photogrammetry tools to develop a three-dimensional model of the environment the drone is flying in. Such model can be stereographic imaging of an object from images acquired by a single camera under different viewing angle and altitudes. A drone can be equipped with two cameras that are looking to the same image under two different angles and reconstruct the depth of the image in real time. The three-dimensional model can also be used with simulations to determine the spread and impact of a gas leak on the immediate environment.

Figure 2:
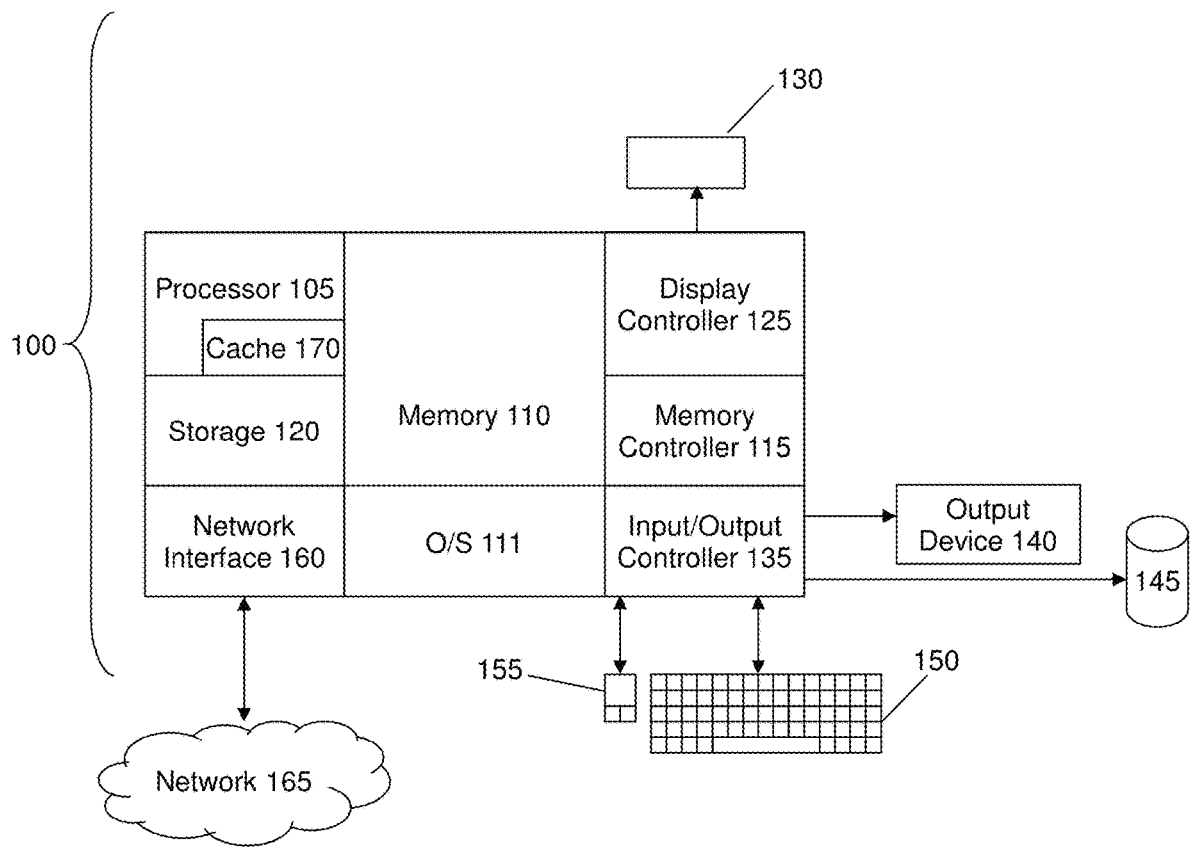
FIG. 2 depicts a block diagram of a controller for a drone in accordance with an embodiment.

FIG. 2 illustrates a block diagram of a controller 100 for use in implementing a system or method according to some embodiments. The systems and methods described herein may be implemented in hardware, software (e.g., firmware), or a combination thereof. In some embodiments, the methods described may be implemented, at least in part, in hardware and may be part of the microprocessor of a special or general-purpose controller 38, such as a personal computer, workstation, minicomputer, or mainframe computer.

In some embodiments, as shown in FIG. 2, the controller 100 includes a processor 105, memory 110 coupled to a memory controller 115, and one or more input devices 145 and/or output devices 140, such as peripheral or control devices that are communicatively coupled via a local I/O controller 135. These devices 140 and 145 may include, for example, battery sensors, position sensors, cameras, microphones and the like. Input devices such as a conventional keyboard 150 and mouse 155 may be coupled to the I/O controller. The I/O controller 135 may be, for example, one or more buses or other wired or wireless connections, as are known in the art. The I/O controller 135 may have additional elements, which are omitted for simplicity, such as controllers, buffers (caches), drivers, repeaters, and receivers, to enable communications.

The I/O devices 140, 145 may further include devices that communicate both inputs and outputs, for instance disk and tape storage, a network interface card (NIC) or modulator/demodulator (for accessing other files, devices, systems, or a network), a radio frequency (RF) or other transceiver, a telephonic interface, a bridge, a router, and the like.

The processor 105 is a hardware device for executing hardware instructions or software, particularly those stored in memory 110. The processor 105 may be a custom made or commercially available processor, a central processing unit (CPU), an auxiliary processor among several processors associated with the controller 38, a semiconductor based microprocessor (in the form of a microchip or chip set), a macroprocessor, or other device for executing instructions. The processor 105 includes a cache 170, which may include, but is not limited to, an instruction cache to speed up executable instruction fetch, a data cache to speed up data fetch and store, and a translation lookaside buffer (TLB) used to speed up virtual-to-physical address translation for both executable instructions and data. The cache 170 may be organized as a hierarchy of more cache levels (L1, L2, etc.).

The memory 110 may include one or combinations of volatile memory elements (e.g., random access memory, RAM, such as DRAM, SRAM, SDRAM, etc.) and nonvolatile memory elements (e.g., ROM, erasable programmable read only memory (EPROM), electronically erasable programmable read only memory (EEPROM), programmable read-only memory (PROM), tape, compact disc read only memory (CD-ROM), disk, diskette, cartridge, cassette or the like, etc.). Moreover, the memory 110 may incorporate electronic, magnetic, optical, or other types of storage media. Note that the memory 110 may have a distributed architecture, where various components are situated remote from one another but may be accessed by the processor 105.

The instructions in memory 110 may include one or more separate programs, each of which comprises an ordered listing of executable instructions for implementing logical functions. In the example of FIG. 2, the instructions in the memory 110 include a suitable operating system (OS) 111. The operating system 111 essentially may control the execution of other computer programs and provides scheduling, input-output control, file and data management, memory management, and communication control and related services.

Additional data, including, for example, instructions for the processor 105 or other retrievable information, may be stored in storage 120, which may be a storage device such as a hard disk drive or solid state drive. The stored instructions in memory 110 or in storage 120 may include those enabling the processor to execute one or more aspects of the systems and methods of this disclosure.

The controller 100 may further include a display controller 125 coupled to a user interface or display 130. In some embodiments, the display 130 may be an LCD screen. In some embodiments, the controller 100 may further include a network interface 160 for coupling to a network 165. The network 165 may be an IP-based network for communication between the controller 38 and an external server, client and the like via a broadband connection. The network 165 transmits and receives data between the controller 38 and external systems. In an embodiment, the external system may be the UAV 20. In some embodiments, the network 165 may be a managed IP network administered by a service provider. The network 165 may be implemented in a wireless fashion, e.g., using wireless protocols and technologies, such as WiFi, WiMax, satellite, etc. The network 165 may also be a packet-switched network such as a local area network, wide area network, metropolitan area network, the Internet, or other similar type of network environment. The network 165 may be a fixed wireless network, a wireless local area network (LAN), a wireless wide area network (WAN) a personal area network (PAN), a virtual private network (VPN), intranet or other suitable network system and may include equipment for receiving and transmitting signals.

Systems and methods according to this disclosure can be embodied, in whole or in part, in computer program products or in controller 100, such as that illustrated in FIG. 2.

Figure 3:
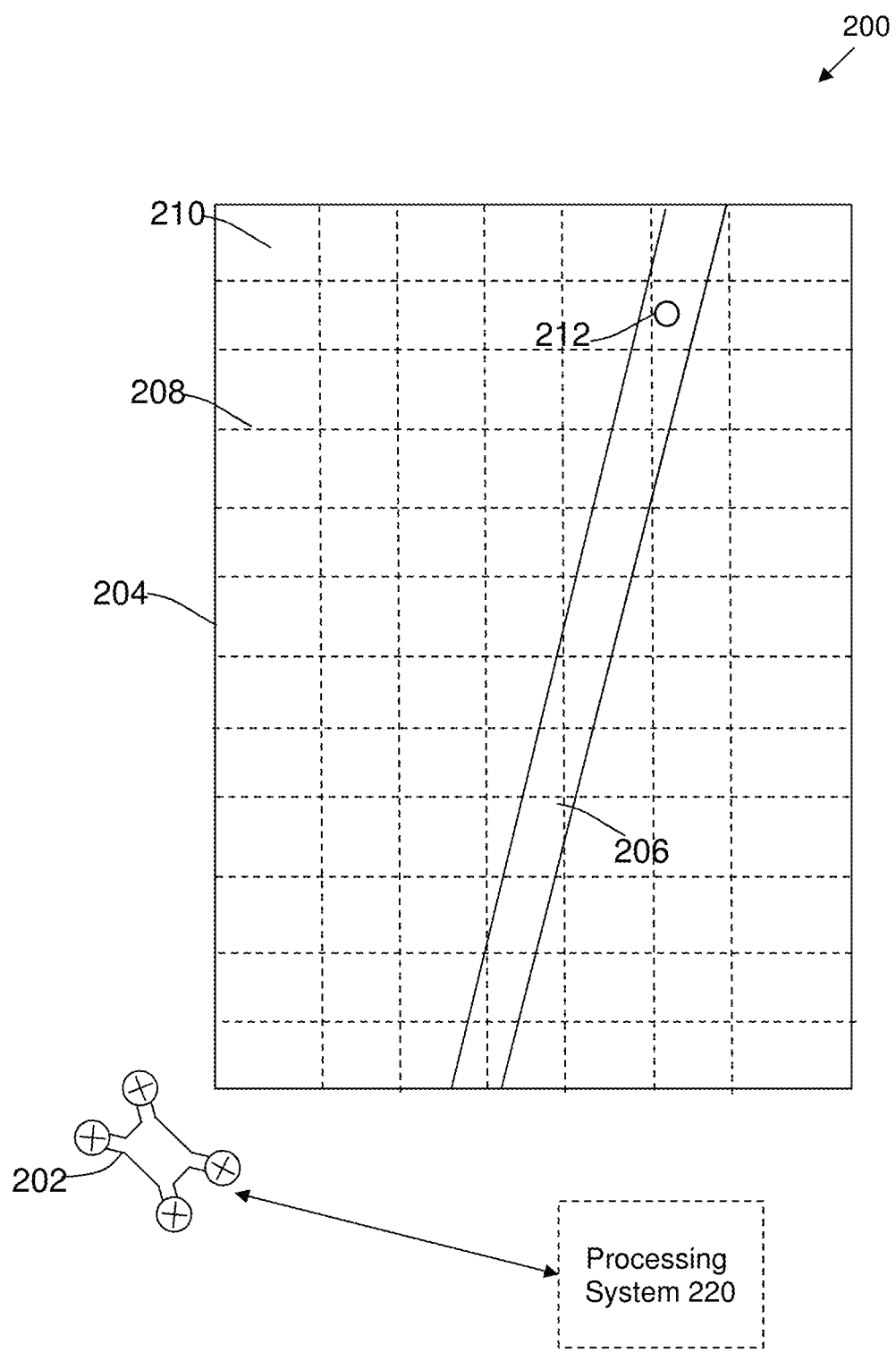
FIG. 3 depicts a plan view of a system for detecting gas leaks using a drone in accordance with an embodiment.

Referring now to FIG. 3, a plan view of a system 200 for detecting gas leaks with a drone 202 in accordance with an embodiment is shown. In exemplary embodiments, the drone 202 is configured to detect a gas leak 212 in a pipeline 206 by flying through a geographic area 204 that includes the pipeline 206. In exemplary embodiments, the drone 202 includes a camera that captures images of the geographic area 204 that are processed with photogrammetry tools to develop a three-dimensional model of the geographic area 204. Such model can be stereographic imaging of an object from images acquired by a single camera under different viewing angle and altitudes. This three-dimensional model of the geographic area 204 can be used to create a flight plan 208 for the drone 202 to follow through the geographic area 204.

In one embodiment, the drone flies along a flight path 208 through a plurality of regions 210 in the geographic area 204 and collects data regarding the presence of gas in the regions 210. For example, the data can include taking infrared images of the region 210 or taking periodic measurements of the concentration of the gas in the region 210. In exemplary embodiments, an infrared camera is used to identify a large area with a presence of methane gas and this identification is corroborated the readings given by the VOC sensor. In some embodiments, the drone 202 can be in communication, either directly or indirectly, with a processing system 220 that is used to process the data collected by the drone 202. In other embodiments, the drone 202 can utilize its onboard processor to process the data collected by the drone 202.

Figure 4A:
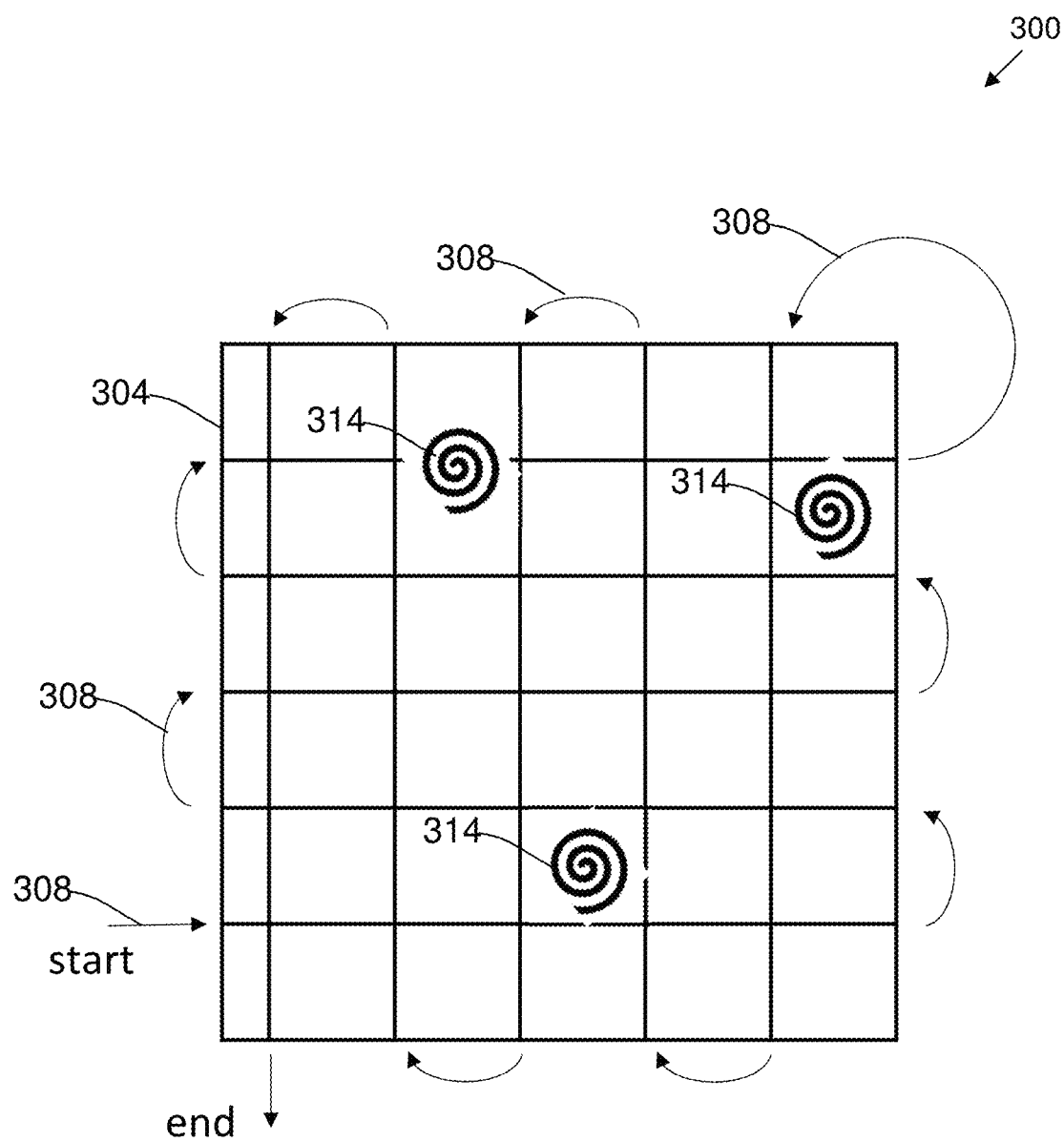
FIGS. 4A and 4B depict a schematic view of a flight plan of a drone for collecting measurement data in accordance with an embodiment.

Referring now to FIG. 4A a schematic view of a flight plan 300 of a drone for collecting measurement data in a geographic area 304 in accordance with an embodiment is shown. In exemplary embodiments, the flight plan 300 includes an initial flight path 308 which includes flying along a grid pattern through the geographic area 304. The drone collects data regarding the presence of gas while flying the initial flight path 308 and identifies one or more regions in the geographic area that include higher than expected concentrations of gas. Secondary flight paths 314 are then created for the one or more regions with the detected gas and the drone flies along the secondary flight paths 314. In exemplary embodiments, the secondary flight paths can include a spiral pattern that is centered around the highest collected concentration of gas detected. The drone collects detailed data regarding the presence of gas while flying along the secondary flight paths 314.

In exemplary embodiments, the drone is configured to capture more detailed information about the presence of gas while flying the secondary flight plan than the initial flight plan, this can include sampling the gas concentration more frequently, sampling the gas concentration with high accuracy sensors, or a combination of both. In one example, the drone only uses an infrared camera to detect the presence of gas while flying the initial flight path and it uses VOC sensors to collect data regarding the presence of gas while flying the secondary flight path.

In exemplary embodiments, the drone can vary its altitude during the initial and secondary flight paths based on the three-dimensional model of the geographic area and/or based on the detected presence of gas in the geographic area. In addition, the drone can use the GPS sensor to tag the location of each gas concentration collected and each image captured. In exemplary embodiments, the altimeter is used to determine the three-dimensional coordinate to match the GPS coordinate. As a result, the concentration of the detected gas can be estimated in a three-dimensional coordinate system.

In exemplary embodiments, while flying along the initial flight path, the drone will evaluate the wind speed and direction and record wind data. The wind speed and direction information will be used by the drone, or another processing system, to predict the location of a possible gas leak and can be used in the calculation of the one or more secondary flight paths. In exemplary embodiments, the wind direction and speed can be extracted from either a wind sensor that is positioned on the ground, from a sensor that is attached to the drone or it can be extracted from the currents that are fed to the engines that rotate the propellers of the drone. In order to maintain the stability of the drone to stay in a still position, the drone needs to apply variable current to the electric motors attached to the blades 24 (FIG. 1). The applied current will try to compensate the wind drag that tries to move the drone from its desired location. The amount of current applied and the pattern in which it is applied to the 4 blades (item 24 in FIG. 1) is a coarse indicator of the wind effect on the drone operation.

In exemplary embodiments, the altitude of the drone can be varied based on the concentration of the gas detected. Once a gas plume is detected, the drone can fly through the gas plume at a slant angle allowing reconstructing the plumes under different weather conditions. Likewise, the flight paths can be carried out at different heights as the plume from the leaks may be moved by the wind. At each height a cross section of the plume concentration can be created. The cross section is going to be modified as the wind direction is changing. In another embodiment, two separate plumes generated by separate sources may be united at a certain height, depending on the wind direction and wind speed. Flying the drone at lower altitudes can separate the two plumes and identify that they are coming from different sources. Cross sectional measurement of the plume distribution at different heights or slanted plains can be created. In one embodiment, the measurements of the concentration of the detected gas can be plugged into a Gaussian model or a computational fluid dynamic model to calculate how the plumes from those sources may be dispersed by the wind. Additionally the plumes may be used to localize the leak or to determine its leak rate using an inversion model.

Figure 4B:
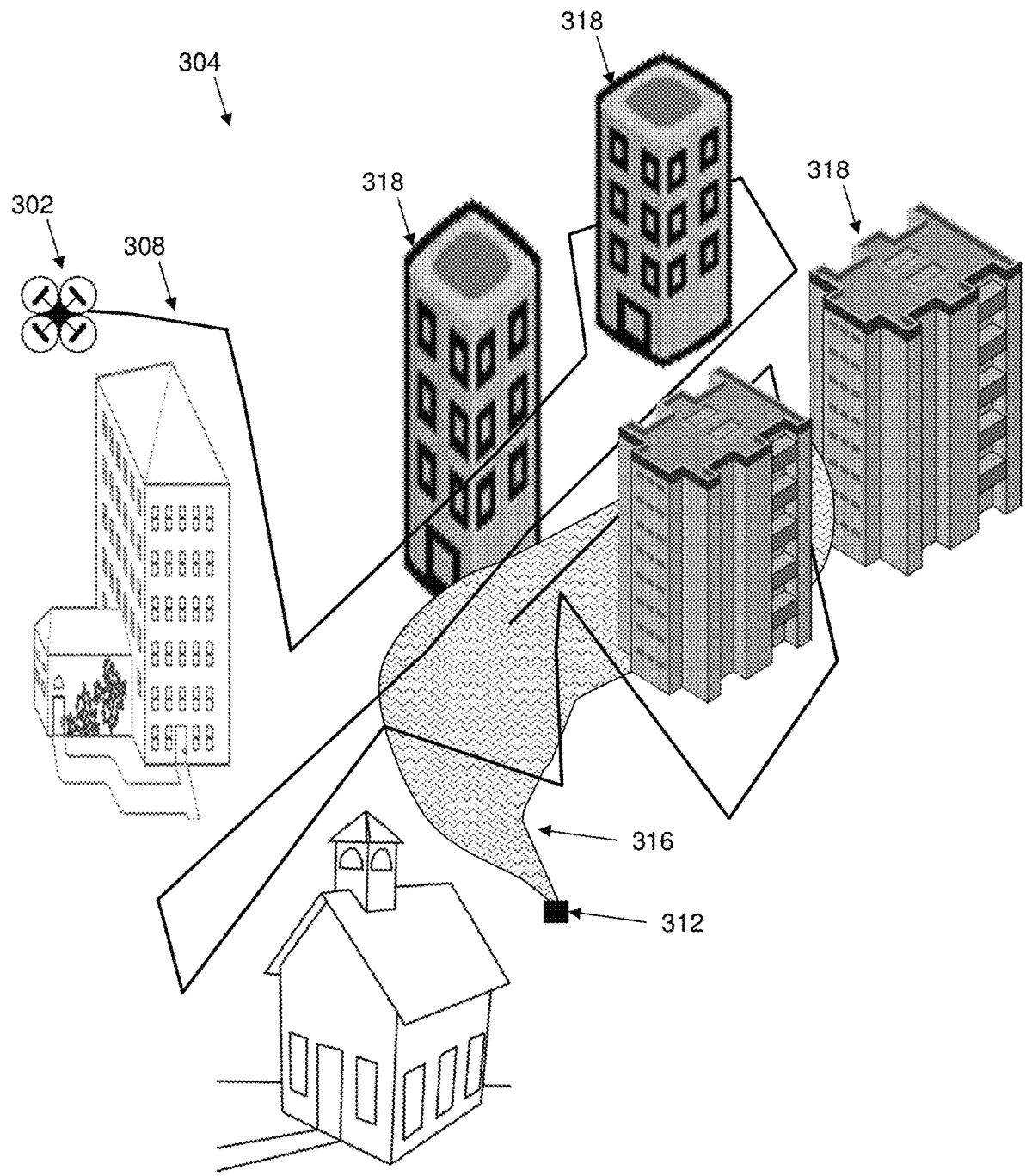

Referring now to FIG. 4B a schematic view of a flight path 308 of a drone 302 for collecting measurement data in a geographic area 304 in accordance with an embodiment is shown. In exemplary embodiments, the flight path 308 is configured to traverse the geographic area 304 while avoiding impacting one or more obstructions 318, such as buildings, in the geographic area 304. In exemplary embodiments, the flight path 308 of the drone 302 includes flying through a gas plume 316 that is formed based on a gas leak 312.

Figure 5:
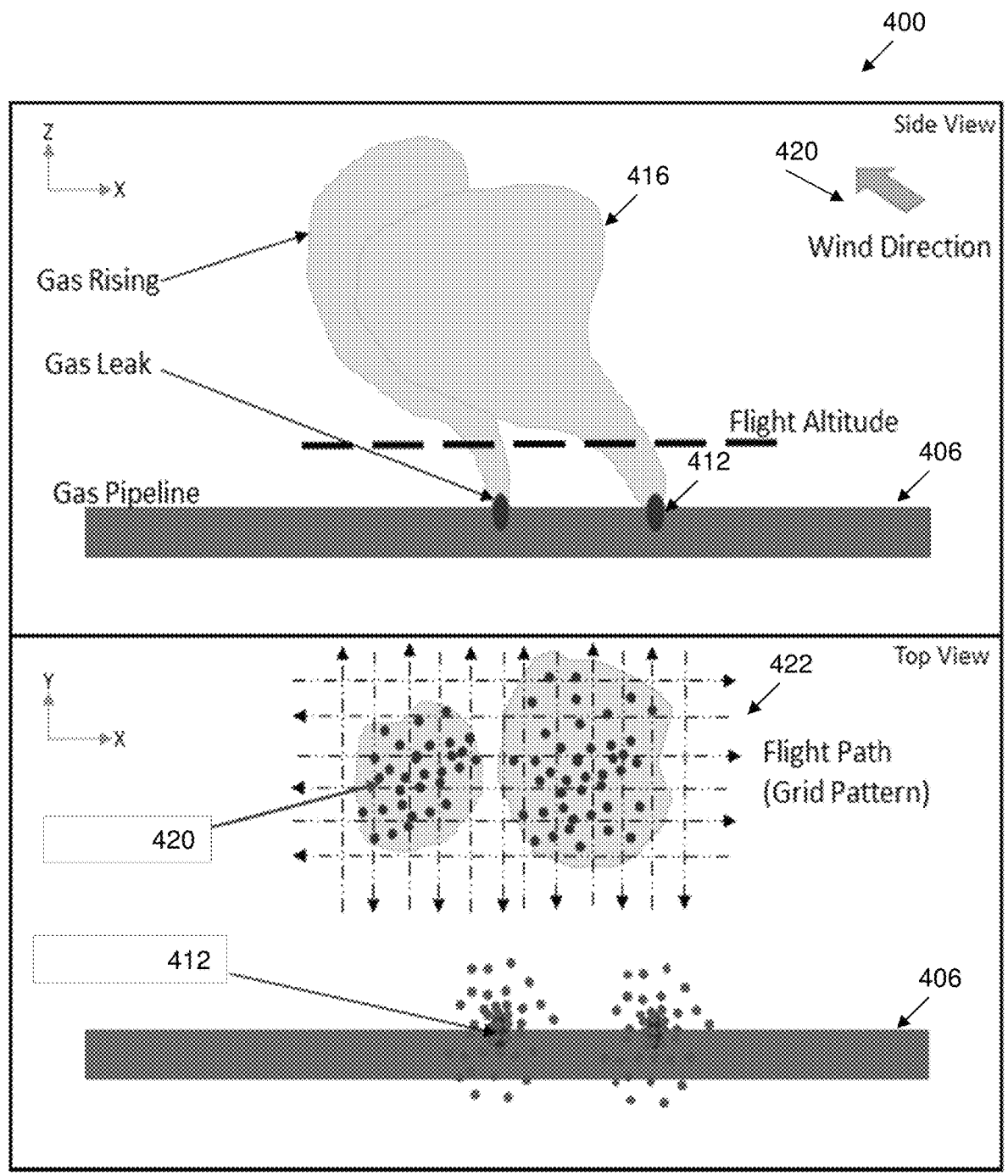
FIG. 5 depicts a schematic view of a model of a gas leak in accordance with an embodiment.

Referring now to FIG. 5 a schematic view of a model 400 of a gas leak in accordance with an embodiment is shown. In an exemplary embodiment, the model 400 can be a three-dimensional model that illustrates one or more gas plumes 416 that are emanating from one or more gas leaks 412 in a pipeline 406. In addition, the model 400 can include an indication of the wind direction 420. In exemplary embodiments, the model 400 can be rendered in a variety of views including, but not limited to a side view and a top view, as shown. In exemplary embodiments, the model 400 can include a rendering of the flight path 422 taken by the drone in collecting the measurements of the gas. We note that gas leaks may have different chemical composition as they can be coming from two different sources (there could be two pipes 406 carrying methane mixed with different ethane concentration or hydrogen sulphide (H2S) concentration). In one embodiment one leak may have prevalently a chemical concentration while the other source may have different chemical composition. The plurality of sensors that are attached to the drone will sense the mixing of the chemicals at different heights from the ground and create concentration maps for each chemical. Using differential measurements the drone will detect the mixing ratio of the two chemical sources and will associate a chemical to the individual sources by acquiring methane plume maps at different heights. Furthermore, the model 400 can include an indication 420 of the detected concentrations of the gas disposed at the corresponding locations.

Figure 6:
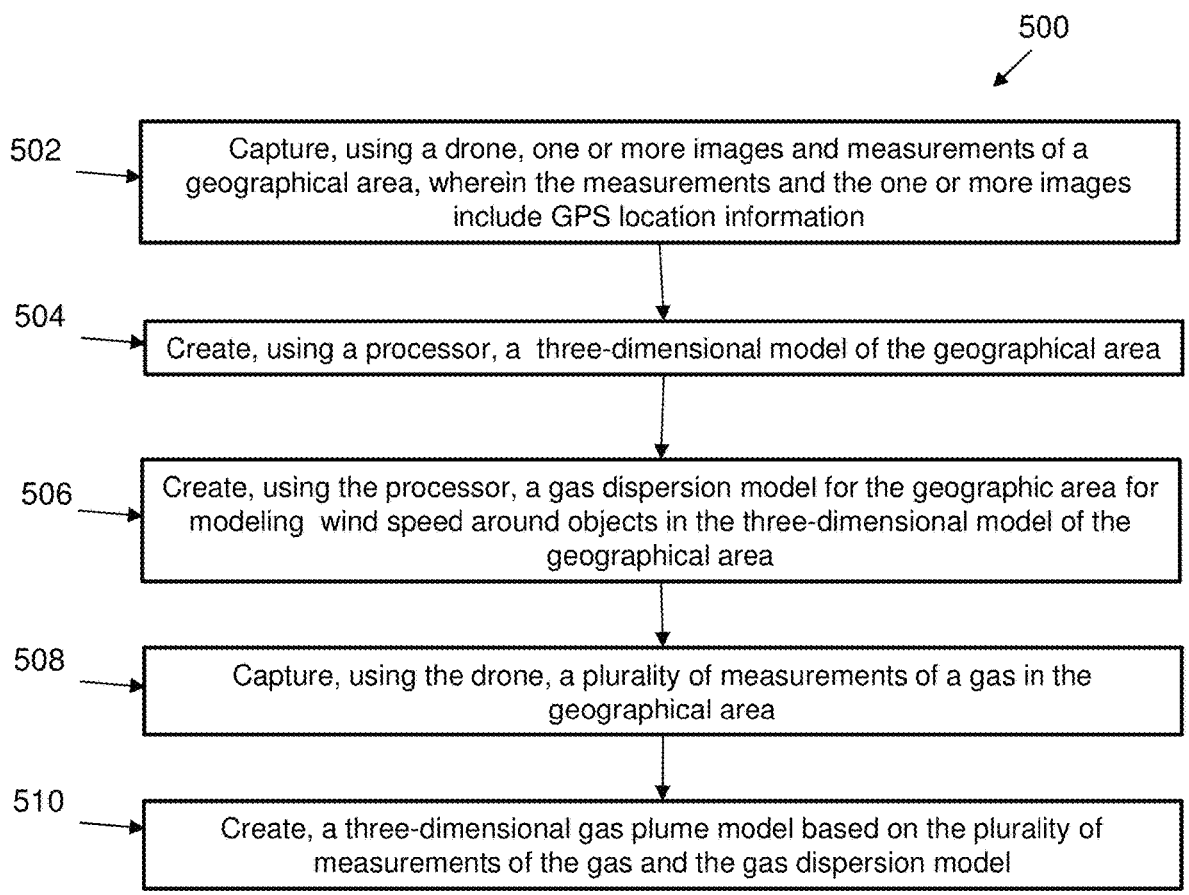
FIG. 6 depicts a flow diagram of a method for detecting gas leaks using a drone in accordance with an embodiment.

Referring now to FIG. 6, a flow diagram of a method 500 for detecting gas leaks using a drone is depicted. As shown at block 502, the method 500 includes capturing, using the drone, one or more images and measurements of a geographical area, wherein the measurements and the one or more images include GPS location information. Next, as shown at block 504, the method includes creating a three-dimensional model of the geographical area.

Many of the existing objects require image acquisition at a different height, different viewing angle, and images acquired at different distances from the boundary of the objects. While images may be acquired using dedicated techniques, an advantage of drone imaging is the ability to quickly integrate changes that occur on the ground and update these images in near real time. This is useful when there are small changes due to constructions, disasters, or nature-induced changes. The images acquired by the drone can be processed with photogrammetry software to produce a three-dimensional mesh of the object. One advantage of having a reconstruction of the scenery is the possibility to avoid during flights those areas. In exemplary embodiments, the drone can be equipped with a high-resolution camera that can acquire images under different angles. The drone may be also equipped with a sensor like an ultrasound sensor, laser, or GPS system.

In one embodiment, to measure accurately dimensions, the drone is positioned at a certain height that may be the height of a building. The drone may send an ultrasound signal and time of flight is acquired. The time of travel is converted to distance and the building location from actual drone location is estimated. The ultrasound signal can be sent under a different angle to reconstruct distance and orientation of the blocking wall that reflect the ultrasound. The ultrasound signal and an image capture can be synchronized such that accurate distances can be assigned to the image reconstruction and create accurate reconstruction of the buildings, infrastructure, and vegetation. Both an acoustic distance estimate and a three-dimensional reconstruction can be extracted from the time of flight and images. Similarly, a laser pulse may be sent toward the ground or wall of a building and time of return is recorded. Or the GPS signal or pressure change as a function of height may be used to estimate the height of the object.

Continuing with reference to FIG. 6, the method 500 also includes creating, using the processor, a gas dispersion model for the geographic area for modeling pollutant gas dispersion around objects in the three-dimensional model of the geographical area, as shown at block 506. To create the plume dispersion the wind distribution around three dimensional objects needs to be modeled to understand how wind is modified or blocked by infrastructure. In exemplary embodiments, the gas dispersion model is created based on the three-dimensional model of the geographical area using a Gaussian model or a computational fluid dynamic model. Both models require as input the wind distribution and measurement of the gas concentration at different points around the area of interest. Next, as shown at block 508, the method 500 includes capturing, using the drone, a plurality of measurements of a gas in the geographical area. In exemplary embodiments, the drone can utilize a method such as the one shown in FIG. 7 to capture the plurality of measurements of a gas in the geographical area. Next, as shown at block 510, the method 500 includes creating, a three-dimensional gas plume model based on the plurality of measurements of the gas and the gas dispersion model.

Figure 7:
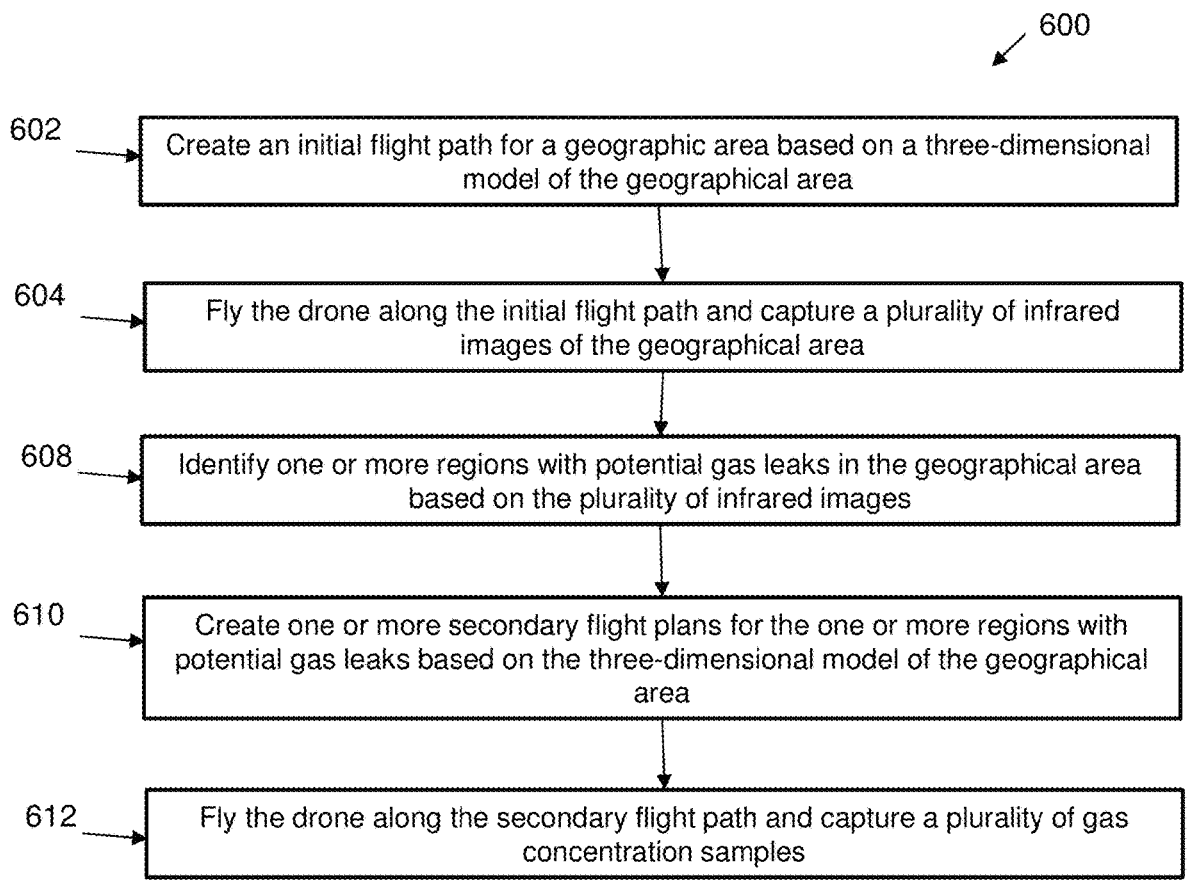
FIG. 7 depicts a flow diagram of a method for monitoring a geographic area for a gas leak using a drone in accordance with an embodiment.

Referring now to FIG. 7, a flow chart illustrating a method 600 for monitoring a geographic area for a gas leak using a drone is shown. As shown at block 602, the method 600 includes creating an initial flight path for a geographic area based on a three-dimensional model of the geographical area. In exemplary embodiments, the initial flight path includes a grid pattern through an entirety of the geographic area and the grid pattern is created based on the three-dimensional model of the geographic area to avoid the drone impacting any objects in the geographic area during flight. Next, as shown at block 604, the method 600 includes flying the drone along the initial flight path and capturing a plurality of infrared images of the geographical area. The method also includes identifying one or more regions with potential gas leaks in the geographical area based on the plurality of infrared images, as shown at block 608. In exemplary embodiments, the plurality of infrared images can be analyzed to determine whether a presence of a gas in an area exceeds a threshold amount. Next, as shown at block 610, the method 600 includes creating one or more secondary flight plans for the one or more regions with potential gas leaks based on the three-dimensional model of the geographical area. In exemplary embodiments, the one or more secondary flight paths includes a spiral pattern through each of the one or more regions. The spiral patterns can be created based on the three-dimensional model of the geographic area to avoid impact with objects in the one or more regions and at the same time minimize the amount of flight while detecting the leak sources. Next, as shown at block 612, the method 600 includes flying the drone along the secondary flight path and capturing a plurality of gas concentration samples. In exemplary embodiments, a plurality of gas concentration samples are collected by a volatile organic compound (VOC) sensor disposed on the drone.

In one embodiment, a method to detect a gas leak based on a sensor equipped unmanned aerial vehicle is provided. The unmanned aerial vehicle includes an infrared camera configured to detect the location and extent of a gas plume. The unmanned aerial vehicle is configured to fly in a grid pattern above that area and will acquire gas concentration measurement using a VOC sensor. The flying grid pattern can be changed dynamically as new rescue objects may appear to avoid collision and allow safe operation of the drone. This is important as in the case of chemical pollution, direct line of sight for drone operation may not be possible and drone may need to switch to autonomous operations where it has to calculate a safe flying route. The unmanned aerial vehicle can acquire imagery at different heights and viewing angles to determine objects in the area using stereographic reconstruction. In exemplary embodiments, the three-dimensional model can be used to identify locations where gas concentration measurements should be carried out due to obstruction and wind flow pattern.

In general, fracking sites are not very well documented regarding construction and infrastructure that are modified from the design moment. By some estimates, these unmonitored and unregulated sites leak a large amount of methane gas every year. A drone system for monitoring gas leaks as described above can be used to create three-dimensional models of the fracking sites and to monitor the fracking sites for gas leaks.

In another embodiment, a drone system for monitoring gas leaks as described above can be used to monitor the presence of a biogas in the area around a farm. The system can be used to establish the pattern of biogas emission, time of the year when emission is high and design a system to capture the biogas as a fuel. In a further embodiment, a drone system for monitoring gas leaks as describe above can be deployed at chemical sites or zones with a potential chemical hazard to detect the presence of various chemicals using a variety of different chemical sensors. Likewise, the system for monitoring gas leaks as described above can be outfitted with a Geiger counter and can be used to detect the presence of radioactive materials in nuclear hazardous zones.

Technical benefits of the methods and systems provided herein include the ability to safely and reliably monitor an area for the presence of a harmful chemical or other material. Once the presence of a harmful chemical or other material is detected, the methods and systems disclosed herein can be used to create three-dimensional models of the harmful chemical or other material and to identify the source and amount of emission of the harmful chemical or other material. In exemplary embodiments, the methods and systems provided herein can detect leaks that are in volume from 0.1 L/hour to 1000 L/hour and distinguish leaks that are separated from each other by a few inches from up to a few mile distance.

It should be appreciated that while embodiments herein refer to a controller 100 as controlling and managing the drone, this is for exemplary purposes and the claims should not be so limited. The analytics can be distributed across multiple computational platforms like mobile devices, laptop computers, cloud based on the computational capabilities of the devices and the timeline required to extract the analytics to run the drone operation. In other embodiments, the controlling and managing of the drone may be performed by a plurality of controllers, a distributed computing environment or a cloud computing environment. It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 8:
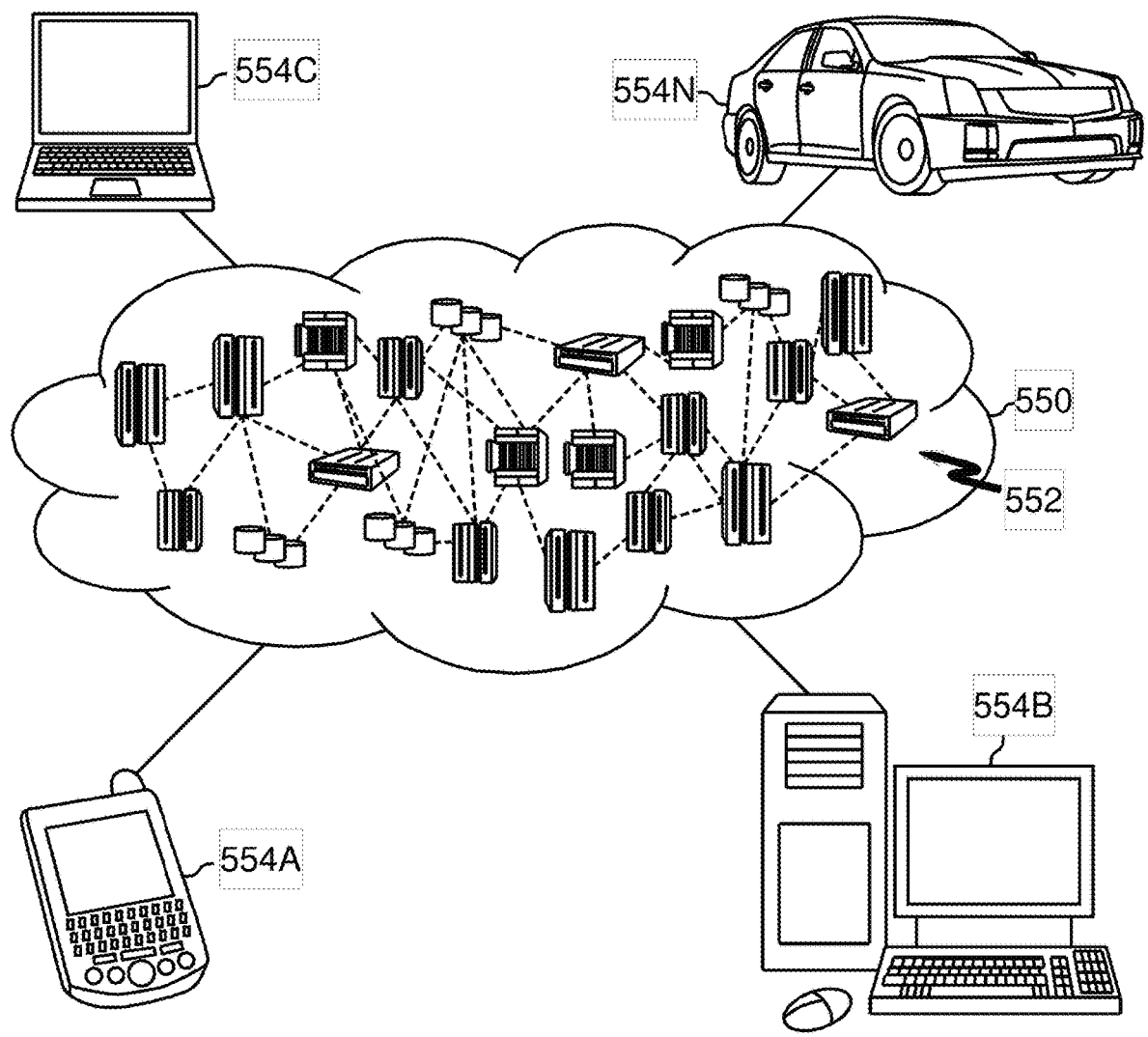
FIG. 8 depicts a cloud computing environment according to an embodiment of the present invention.

Referring now to FIG. 8, illustrative cloud computing environment 550 is depicted. As shown, cloud computing environment 550 comprises one or more cloud computing nodes 552 with which local computing devices used by cloud consumers, such as, for example, personal digital assistant (PDA) or cellular telephone 554A, desktop computer 554B, laptop computer 554C, and/or automobile computer system 554N may communicate. Nodes 552 may communicate with one another. They may be grouped (not shown) physically or virtually, in one or more networks, such as Private, Community, Public, or Hybrid clouds as described hereinabove, or a combination thereof. This allows cloud computing environment 550 to offer infrastructure, platforms and/or software as services for which a cloud consumer does not need to maintain resources on a local computing device. It is understood that the types of computing devices 554A-N shown in FIG. 8 are intended to be illustrative only and that computing nodes 552 and cloud computing environment 550 can communicate with any type of computerized device over any type of network and/or network addressable connection (e.g., using a web browser).

Figure 9:
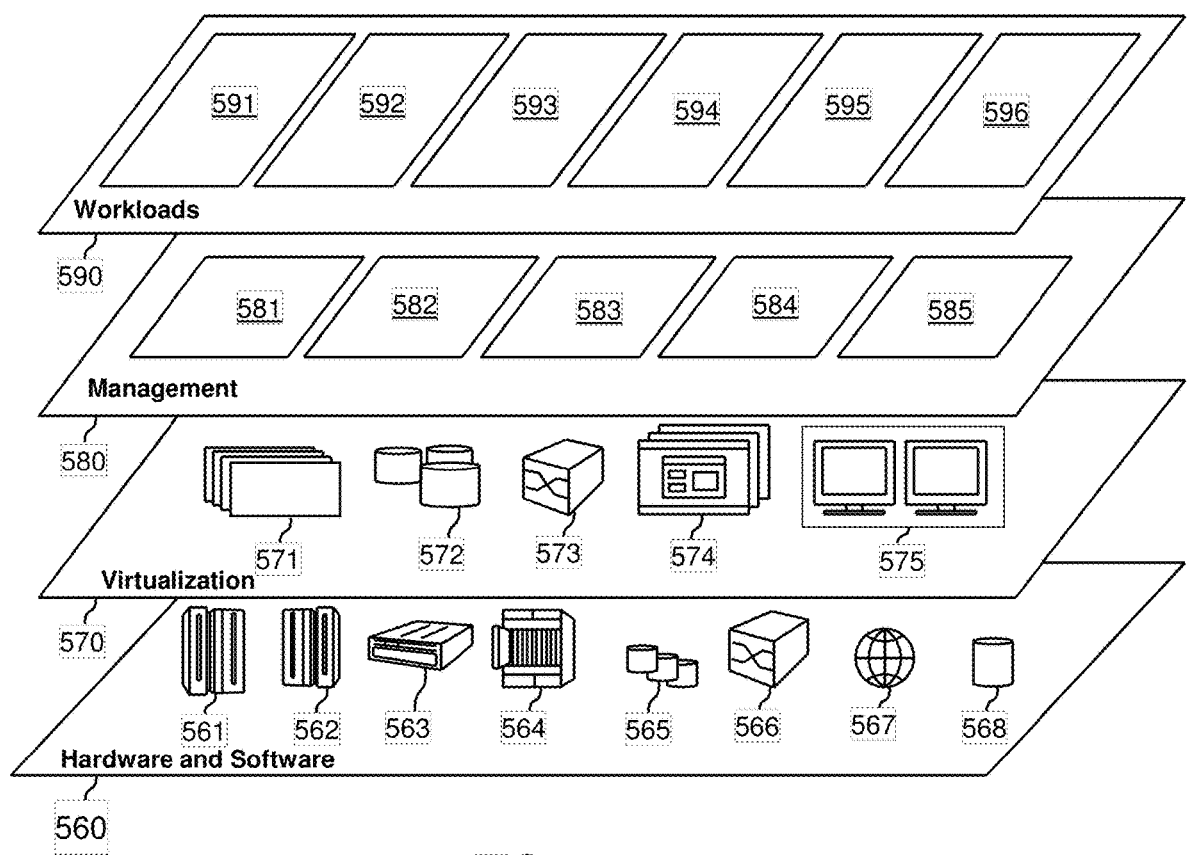
FIG. 9 depicts abstraction model layers according to an embodiment of the present invention.

Referring now to FIG. 9, a set of functional abstraction layers provided by cloud computing environment 550 (FIG. 8) is shown. It should be understood in advance that the components, layers, and functions shown in FIG. 9 are intended to be illustrative only and embodiments of the invention are not limited thereto. As depicted, the following layers and corresponding functions are provided:

Hardware and software layer 560 includes hardware and software components. Examples of hardware components include: mainframes 561; RISC (Reduced Instruction Set Computer) architecture based servers 562; servers 563; blade servers 564; storage devices 565; and networks and networking components 566. In some embodiments, software components include network application server software 567 and database software 568.

Virtualization layer 570 provides an abstraction layer from which the following examples of virtual entities may be provided: virtual servers 571; virtual storage 572; virtual networks 573, including virtual private networks; virtual applications and operating systems 574; and virtual clients 575.

In one example, management layer 580 may provide the functions described below. Resource provisioning 581 provides dynamic procurement of computing resources and other resources that are utilized to perform tasks within the cloud computing environment. Metering and Pricing 582 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 583 provides access to the cloud computing environment for consumers and system administrators. Service level management 584 provides cloud computing resource allocation and management such that required service levels are met. Service Level Agreement (SLA) planning and fulfillment 585 provides pre-arrangement for, and procurement of, cloud computing resources for which a future requirement is anticipated in accordance with an SLA.

Workloads layer 590 provides examples of functionality for which the cloud computing environment may be utilized. Examples of workloads and functions which may be provided from this layer include: mapping and navigation 591; software development and lifecycle management 592; virtual classroom education delivery 593; data analytics processing 594; transaction processing 595; and a UAV positioning and monitoring management 596. The UAV positioning and monitoring management 596 may perform one or more methods for detecting gas leaks using a drone, such as but not limited to the methods described in reference to FIG. 6 and FIG. 7 for example.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method for detecting gas leaks using a drone, the method comprising:
    creating, by the drone, an initial flight path based on a three-dimensional model of a geographic area;
    capturing, by the drone, a first set of data regarding a presence of a gas in the geographic area while flying along the initial flight path through the geographic area;
    creating one or more secondary flight paths through one or more regions in the geographic area in which the presence of the gas exceeds a threshold amount;
    capturing, by the drone, a second set of data regarding a concentration of the gas in the one or more regions while flying along the one or more secondary flight paths;
    capturing, by the drone, wind data in the geographic area while flying along the initial flight path and the one or more secondary flight paths; and
    creating a three-dimensional gas plume model for gas leaks identified in the geographic area based on the first set of data, the second set of data, and the wind data, wherein the three-dimensional gas plume model identifies a location of a source of the gas leaks,
    wherein the first set of data is captured at a first sampling rate using a sensor, and the second set of data is captured at a second sampling rate using the sensor, the second sampling rate being greater than the first sampling rate.

2. The computer-implemented method of claim 1, wherein the three-dimensional model of the geographic area is created based on a plurality of global positioning system (GPS) tagged images and measurements of objects in the geographic area captured by the drone.

3. The computer-implemented method of claim 2, wherein the initial flight path includes a grid pattern through an entirety of the geographic area, wherein the grid pattern is created based on the three-dimensional model of the geographic area to avoid impact with objects in the geographic area.

4. The computer-implemented method of claim 2, wherein the one or more secondary flight paths includes a spiral pattern through each of the one or more regions.

5. The computer-implemented method of claim 4, wherein the spiral pattern is created based on the three-dimensional model of the geographic area to avoid impact with objects in the one or more regions.

6. The computer-implemented method of claim 1, wherein the second set of data regarding the concentration of the gas in the geographic area includes a plurality of gas concentrations captured by a volatile organic compound (VOC) sensor disposed on the drone.

7. The computer-implemented method of claim 1, wherein the first set of data regarding the presence of the gas in the geographic area includes a plurality of infrared images of the geographic area captured by the drone.

8. The computer-implemented method of claim 1, wherein the initial flight path includes a grid pattern through an entirety of the geographic area, wherein the grid pattern is configured to avoid obstructions based on the three-dimensional model of the geographic area.

\* \* \* \* \*